United States Patent
Brown et al.

(10) Patent No.: US 7,362,097 B2
(45) Date of Patent: Apr. 22, 2008

(54) RFT PIPELINE INSPECTION SYSTEM AND METHOD THEREFOR

(75) Inventors: David J. Brown, Enumclaw, WA (US); John Hugo Stout, Buckeye, AZ (US)

(73) Assignee: Arizona Public Service Company, Phoenix, AZ (US)

( * ) Notice: Subject to any disclaimer, the term of this patent is extended or adjusted under 35 U.S.C. 154(b) by 372 days.

(21) Appl. No.: 11/175,093

(22) Filed: Jul. 5, 2005

(65) Prior Publication Data

US 2007/0006670 A1    Jan. 11, 2007

(51) Int. Cl.
G01N 27/72    (2006.01)

(52) U.S. Cl. ..................................... 324/220

(58) Field of Classification Search ............. 324/220
See application file for complete search history.

(56) References Cited

U.S. PATENT DOCUMENTS

| | | | |
|---|---|---|---|
| 4,218,651 A * | 8/1980 | Ivy | ........................... 324/227 |
| 4,647,849 A | 3/1987 | Strickland et al. | |
| 4,855,676 A | 8/1989 | Cecco et al. | |
| 5,210,492 A | 5/1993 | Hosohara et al. | |
| 5,365,169 A | 11/1994 | Hosohara et al. | |
| 5,454,276 A | 10/1995 | Wernicke | |
| 5,461,312 A | 10/1995 | Hosohara et al. | |
| 5,623,203 A | 4/1997 | Hosohara et al. | |
| 5,675,251 A | 10/1997 | MacLean et al. | |
| 5,821,747 A | 10/1998 | Atherton et al. | |
| 6,002,251 A | 12/1999 | Sun | |
| 6,087,830 A | 7/2000 | Brandley et al. | |
| 6,127,823 A | 10/2000 | Atherton | |
| 6,271,670 B1 | 8/2001 | Caffey | |
| 6,359,434 B1 | 3/2002 | Winslow et al. | |
| 6,456,066 B1 | 9/2002 | Burd et al. | |
| 6,474,165 B1 | 11/2002 | Harper et al. | |
| 6,487,922 B1 | 12/2002 | Bauer et al. | |
| 6,556,927 B1 | 4/2003 | Latta | |
| 6,583,618 B2 | 6/2003 | McClelland | |
| 6,636,037 B1 | 10/2003 | Ou-Yang | |
| 6,762,602 B1 | 7/2004 | Laursen | |
| 6,781,369 B2 | 8/2004 | Paulson et al. | |
| 6,791,318 B2 | 9/2004 | Paulson et al. | |
| 6,823,269 B2 | 11/2004 | Junker et al. | |
| 2003/0057943 A1 | 3/2003 | McClelland | |

(Continued)

*Primary Examiner*—Robert Raevis
(74) *Attorney, Agent, or Firm*—Jordan M. Meschkow; Lowell W. Gresham; Charlene Jacobsen

(57) ABSTRACT

A system (20) and method for the inspection of a pipeline (22) is disclosed. The system (20) is made up of a plurality of flexibly coupled modular units (24) configured to pass through the pipeline (22). One modular unit (24) is a tractor unit (40) configured to propel the system (20) through the pipeline (22). Another modular unit (24) is an RFT transmission unit (42) with an excitation coil (58) configured to excite a magnetic field (112) within the pipeline (22). A third modular unit (24) is an RFT reception unit (46) incorporating a pair of adjacent differentially connected reception coils (80) and a differential instrumentation amplifier (100) affixed to a rotational mount (78). A fourth modular unit (24) is a motor unit (44) incorporating a motor (66) which rotates the rotational mount (78). The pair of reception coils (80) detects the magnetic field (112) and produces a differential detection signal which is then amplified and analyzed. An electrical cable (106) is used to provide power and/or signals to/from the system.

22 Claims, 5 Drawing Sheets

U.S. PATENT DOCUMENTS

2004/0112152 A1 6/2004 Stout et al.
2004/0217759 A1 11/2004 Burkhardt et al.
2004/0243321 A1 12/2004 Pittalwala et al.

* cited by examiner

RFT PIPELINE INSPECTION SYSTEM AND METHOD THEREFOR

TECHNICAL FIELD OF THE INVENTION

The present invention relates to the field of pipeline inspection systems. More specifically, the present invention relates to the field of pipeline inspection systems utilizing remote-field testing (RFT) techniques.

BACKGROUND OF THE INVENTION

In non-destructive testing of tubular metal products, two techniques are employed by a vast number of testing systems. These two techniques are eddy-current testing and remote-field testing. While these techniques are often confused with each other, particularly by those familiar with only one of the two techniques, they are vastly different from each other.

In eddy-current inspection systems, a magnetic field is imposed upon the tubular metal product under test. This magnetic field generates eddy currents within the tubular metal product. Cracks or other flaws in the tubular metal product may produce disturbances in these eddy currents. These disturbances may then be detected by the appropriate sensors.

Ferromagnetic materials, e.g., steel and iron, tend to rapidly swamp out eddy currents due to the formation of strong secondary magnetic fields. Therefore, eddy-current systems are best suited for tubular metal products fabricated of non-ferromagnetic conductive materials, e.g., stainless steel, brass, copper.

With tubular metal products fabricated of non-ferromagnetic materials, the primary magnetic field is confined to the immediate area surrounding the excitation coil(s). This necessitates a close-order detection of the primary magnetic field. Such a close-order detection system would have its sensors proximate where the eddy-current field is strongest. Eddy-current systems often take advantage of this close-order operation by providing both excitation and detection within a single unit.

In addition, eddy-current techniques require that the sensors be in near physical contact, i.e., within 1.25 mm (0.05 inch), of the inner wall of the tubular metal product. This proximity may lead to problems in negotiating curves and/or fittings, and when encountering debris within the tubular metal product. For this reason, eddy-current systems are often limited to the inspection of new (i.e., clean) tubular metal products, especially those have long and substantially straight sections.

Remote-field testing (RFT) inspection systems, on the other hand, depend upon the detection of distortions of the primary magnetic field as it passes through the pipe wall again at the receiving coils at two or more pipe diameters distance. This allows the RFT sensors to detect the primary magnetic field beyond the range of eddy current effects that may interact and produce false errors. RFT systems are therefore best suited for use with tubular metal products fabricated of ferromagnetic materials.

In a typical RFT system, the primary magnetic field is toroidal, with the outer surface of the torus constrained by the ferromagnetic tubular metal product and the inner surface of the torus (i.e., the "hole" well within the inner surface of the tubular metal product). This allows the RFT system to sense distortions in the magnetic field well within the inner surface of the tubular metal product. Therefore, a greater clearance between various units of an RFT system is allowable than with the units of an eddy-current system. This allows for greater negotiability of the tubular metal product through curves and fitting and over debris. RFT systems are therefore better suited for tubular metal products that are not new (i.e., dirty).

A problem exists with RFT inspection systems in that small flaws that are inline with the lines of flux of the primary magnetic field tend to be nearly undetectable. For example, a longitudinal flaw will cause very little perturbation in a longitudinal field.

A weak perturbation, such as that of a longitudinal flaw in a longitudinal field, can be made more apparent by scanning across the field rather than with the field, i.e., scanning latitudinally in a longitudinal field. This poses several electrical and mechanical problems not readily addressed by traditional RFT systems.

Another problem exists with RFT systems in that the detection of the primary magnetic field at a reasonable distance from the excitation coils, in order to be beyond the range of eddy-current effects, results in a relatively weak detection signal. This weak signal is more susceptible to noise contamination than the signals detected by traditional eddy-current systems.

Since a preponderance of tubular metal products are fabricated of ferromagnetic materials, it is desirable that an RFT system be provided that detects latitudinal, longitudinal, and point flaws in a tubular metal product while producing a robust and reliable detection signal.

SUMMARY OF THE INVENTION

Accordingly, it is an advantage of the present invention that a remote-field testing (RFT) pipeline inspection system and method of operation thereof are provided.

It is another advantage of the present invention that an RFT inspection system is provided that detects latitudinal, longitudinal, and point flaws in a pipeline.

It is another advantage of the present invention that an RFT inspection system is provided that provides a robust detection signal.

The above and other advantages of the present invention are carried out in one form by a system for inspecting a pipeline having an inner diameter d, where the system incorporates a plurality of modular units configured to pass through the pipeline, with each modular unit flexibly coupled to an adjacent modular unit, and wherein the plurality of modular units includes an RFT transmission unit incorporating an excitation coil substantially concentric with the pipeline and configured to excite a magnetic field within the pipeline, and an RFT reception unit incorporating a plurality of reception coils configured to rotate relative to the excitation coil and configured to detect the magnetic field within the pipeline at a reception distance D from the excitation coil, where $D \geq 2d$.

The above and other advantages of the present invention are carried out in another form by an RFT method of inspecting a pipeline having an inner diameter d, where the method includes forming an inspection system of a plurality of modular units configured to pass through the pipeline, where the forming activity includes establishing a tractor unit configured to provide motive power for the inspection system as one of the modular units, arranging a transmission unit with an excitation coil substantially concentric with the pipeline as one of the modular units, instituting a reception unit with a plurality of reception coils as one of the modular units, and flexibly coupling the modular units to form the inspection system so that the reception coils are at a reception distance D from the excitation coil, where $2d \leq D \leq 3d$; coupling an electrical cable to one of the modular units; insinuating the inspection system into the pipeline; providing electrical power to the tractor unit through the electrical cable; propelling the inspection system through the pipeline using the motive power of the tractor unit; exciting the excitation coil to produce the magnetic field within the pipeline; rotating the reception coils relative to the excitation coil; detecting the magnetic field; producing a detection signal in response to the magnetic field; amplifying the detection signal to produce a robust detection signal; and analyzing the robust detection signal.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Those skilled in the art will appreciate that the term "pipeline," as used in this discussion, refers generically to any tubular metal product, and that the pipeline may also include non-metallic components.

Figure 1:
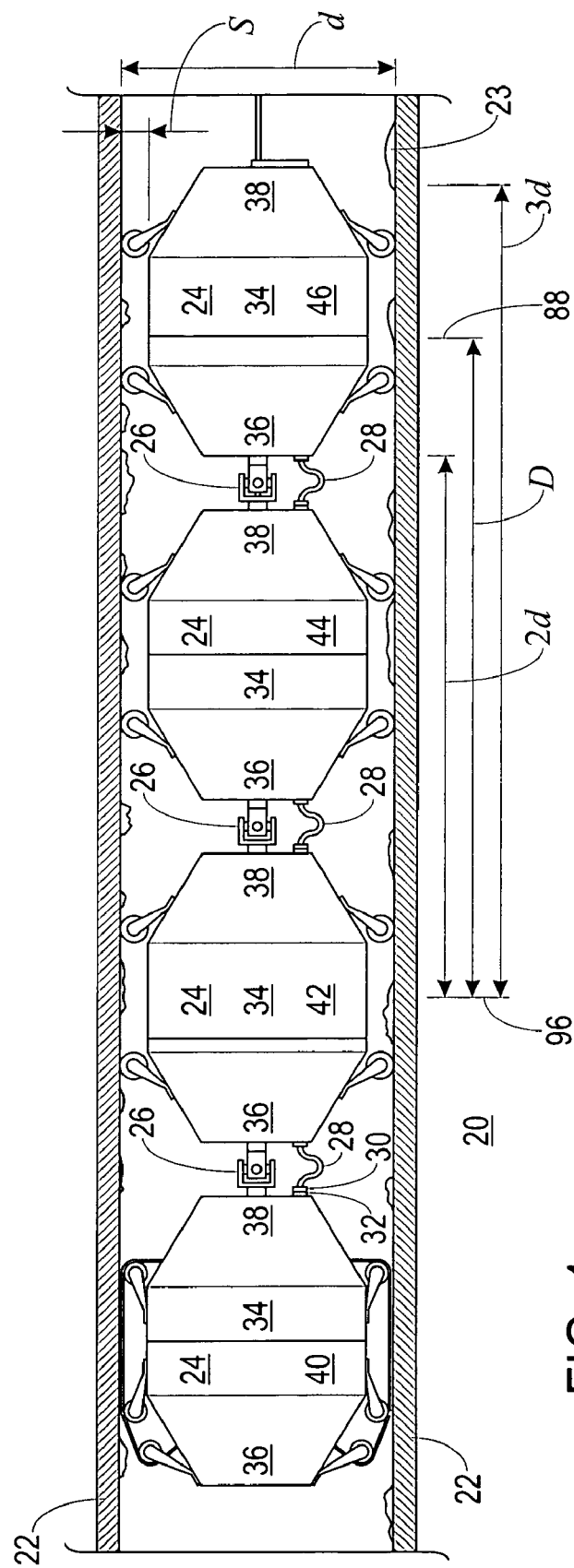
FIG. 1 shows a simplified view of an inspection system within a pipeline in accordance with a preferred embodiment of the present invention.

FIG. 1 shows a simplified view of an inspection system 20 within a pipeline in accordance with a preferred embodiment of the present invention. The following discussion refers to FIG. 1.

This discussion discloses inspection system 20 for use in the non-destructive inspection of pipelines 22 using remote-field testing (RFT) methodology. For clarity and simplification, common components well known to those skilled in the art, e.g., fasteners, bearings, and the like, have been omitted from this discussion. Additionally, this discussion is divided into two parts: the structure of system 20; and the operation of system 20.

Structure of RFT Inspection System

As may be seen in FIG. 1, RFT inspection system 20 is made up of a plurality of modular units 24 configured to pass through pipeline 22. Those skilled in the art will appreciate that the term "modular" is not synonymous with the term "interchangeable." Indeed, in the four-unit embodiment of system 20 exemplified in FIG. 1, each modular unit 24 is different in both construction and operation.

It is not a requirement of the present invention, however, that all modular units 24 be different in all embodiments. In other embodiments of system 20, two or more modular units 24 may be substantially identical without departing from the spirit of the present invention.

Modular units 24 are flexibly coupled to each other to form a train of modular units 24. That is, each modular unit 24 is coupled to adjacent modular unit(s) 24 by a flexible coupling 26. The use of flexible couplings 26 allows system 20 to negotiate curves, fittings, and debris #23 (i.e., dirt, sludge, etc.) within pipeline 22. The use of flexible couplings 26 also assures that non-adjacent modular units 24 are flexibly coupled to each other through intervening modular unit(s) 24.

In the Figures, flexible couplings 26 are exemplified as universal couplings. The use of universal couplings is not a requirement of the present invention. Other flexible couplings known to those skilled in the art may be used without departing from the spirit of the present invention.

Desirably, flexible couplings 26 are detachable couplings, i.e., capable of being attached to and detached from either or both of the coupled modular units 24. By using detachable couplings for flexible couplings 26, the insertion and extraction of system 20 into and out of pipeline 22 is greatly facilitated. To wit, the first modular unit 24 may be inserted into pipeline 22, then the second modular unit 24 may be coupled to the first modular unit 24 and inserted into pipeline 22, and so forth until the last modular unit 24 has been inserted into pipeline 22. In this manner, the individual doing the inserting need handle only one modular unit 24 at a time.

Modular units 24 are also electrically connected to each other. This is accomplished by flexible and detachable electrical couplings 28. In the preferred embodiments of the Figures, electrical couplings 28 are depicted as fixedly coupled to the following modular unit 24 and detachably coupled to the leading modular unit 24 through a plug 30 and receptacle 32. Additionally, electrical couplings 28 are depicted as offset from the centers of modular units 24. This is desirable in order to make the connection of modular units 24 more easily accomplished during the insertion of modular units 24 into pipeline 22. However, this implementation of electrical couplings 28 is not a requirement of the present invention. Those skilled in the art will appreciate that, in another embodiment, electrical coupling 28 could be made a part of flexible coupling 26. The use of other forms of electrical connection between modular units 24 does not depart from the spirit of the present invention.

Those skilled in the art will appreciate that electrical couplings 28 desirably consist of a suitably shielded cable, plus requisite fittings, so as to minimize interference with signals within modular units 24 and within electrical couplings 28 themselves.

Each modular unit 24 has a substantially rigid body 34. Modular units 24 act like a string of beads within pipeline 22. For this reason, it is desirable that modular units 24 have tapered front and rear ends 36 and 38 to better negotiate curves, fittings, and debris #23 within pipeline 22.

It is desirable that modular units 24 clear the inside wall of pipeline 22 by a distance S of at least 12.5 mm (0.5 inch) to facilitation negotiation through pipeline 22. This means that excitation and reception coils (discussed hereinafter) are greater than 12.5 mm (0.5 in) from an inner wall of pipeline 22.

FIG. 1 depicts an exemplary four-unit embodiment of RFT inspection system 20, being a typical system 20 with modular units 24 separated by function. In this embodiment, system 20 incorporates a tractor unit 40, an RFT transmission unit 42, a motor unit 44, and an RFT reception unit 46.

The number of actual modular units 24 in system 20 may vary depending upon the specific embodiment of system 20 in use. For example, an alternative six-unit embodiment may contain tractor unit 40, transmission unit 42, a second tractor unit 40, reception unit 46, a dummy unit (not shown), and motor unit 44. This alternative embodiment has the advantage of separating motor unit 44 from reception unit 46, which is desirable for noise reduction (discussed hereinafter).

In some embodiments, tractor unit 40 and/or motor unit 44 may be combined with transmission unit 42 in the same physical modular unit 24. This is possible because transmission unit 42 is relatively insensitive to the electrical noise produced by tractor unit 40 and/or motor unit 44. Conversely, reception unit 46 is more susceptible to electrical noise than transmission unit 42. Therefore, it is desirable that neither tractor unit 40 nor motor unit 44 be combined with reception unit 46. Electrical noise is discussed in greater detail hereinafter.

Those skilled in the art will appreciate that the number of modular units 24 that make up a given embodiment of system 20 is not a requirement of the present invention. Other embodiments (not shown) are practical. For example, an embodiment may have dual transmission units 42 positioned on either side of a single reception unit 46. Similarly, an embodiment may have dual reception units 46 positioned on either side of single transmission unit 42. Variations in the number and combinations of modular units 24 do not depart from the spirit of the present invention.

Figure 2:
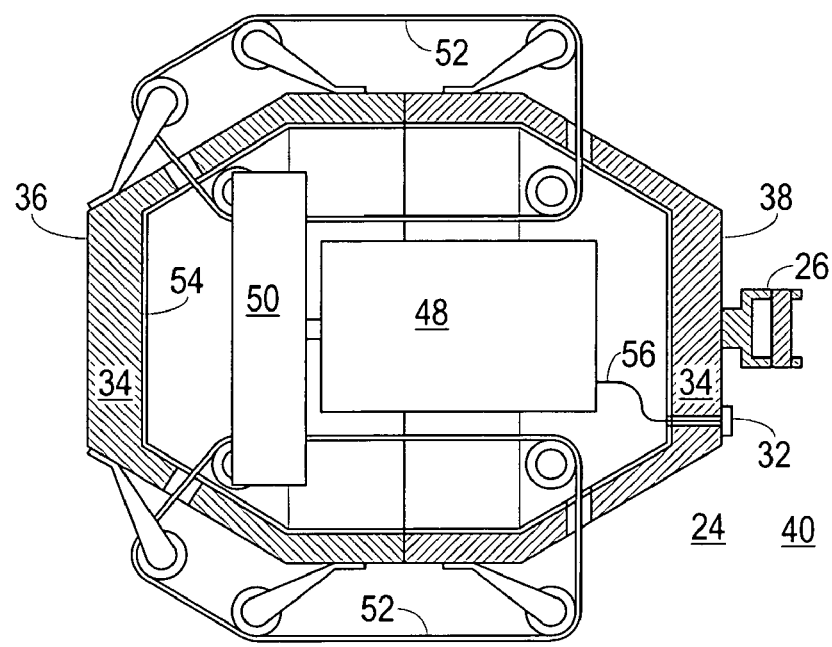
FIG. 2 shows a simplified cross-sectional view of a tractor unit for the inspection system of FIG. 1 in accordance with a preferred embodiment of the present invention.

FIG. 2 shows a simplified cross-sectional view of an exemplary tractor unit 40 for RFT inspection system 20 in accordance with a preferred embodiment of the present invention. The following discussion refers to FIGS. 1 and 2.

Tractor unit 40 provides motive power for system 20. In the preferred embodiment, tractor unit 40 may contain one or more drive motors 48 which may coupled through one or more transmissions 50 to drive a plurality of caterpillar treads 52. Only two sets of caterpillar treads 52 are shown for clarity, but any number of sets of caterpillar treads 52 may be used by tractor unit 40.

Drive motor 48 desirably provides tractor unit 40 with the ability to negotiate system 20 through various turns and couplings of pipeline 22. Also desirable, but not a requirement of the present invention, is the ability to reverse drive motor 48 to back-up system 20, in the event of an obstruction or jam.

Because drive motor 48 is a potential source of electrical noise (discussed in more detail hereinafter), it is desirable that tractor unit 40 be shielded. In one approach to shielding, tractor unit 40 may be lined with a conductive shield 54. By being conductive, shield 54 limits severely the amount of electronic noise radiated into pipeline by drive motor 48.

If shield 54 is also formed of magnetically conductive material, such as Mumetal, then magnetic fields generated by drive motor 48 may also be constrained from entering pipeline 22. This is desirable, as magnetic fields induced by drive motor 48 may interfere with the magnetic field (discussed hereinafter) introduced into pipeline 22 by transmission unit 42.

In other embodiments (not shown), additional devices (e.g., a motor control circuit or a nose-mounted camera) may be incorporated without departing from the spirit of the present invention.

Those skilled in the art will appreciate that tractor unit 40, as depicted and discussed herein, is not a requirement of the present invention. Other tractor units 52 using wheels rather than caterpillar treads 52 may be substituted for tractor unit 40. Similarly, other devices to provide motive power to system 20, e.g., a tow line, may be used without departing from the spirit of the present invention.

Power and/or signals for tractor unit 40 pass through receptacle 32. Intra-unit wiring 56 couples receptacle 32 to drive motor 48 and any other electrical/electronic devices within tractor unit 40. In the preferred embodiment, drive motor 48 is fed 220 volts AC. This is not a requirement of the present invention. Other voltages and/or DC may be used without departing from the spirit of the present invention.

Desirably, intra-unit wiring 56 is suitably shielded to limit electrical interference with signals present in modular units 24 and in intra-unit wiring 56 itself.

In FIG. 1, tractor unit 40 is the first modular unit 24 and pulls the other modular units 24 after it. As the first modular unit 24, tractor unit 40 has flexible coupling 26 only upon rear end 38. Using tractor unit 40 as the first modular unit 24 is typical, but is not a requirement of the present invention. For example, in an alternative embodiment tractor unit 40 may be the second modular unit 24, thereby pushing the first modular unit 24 ahead of it and pulling the other modular units after it. In this alternative embodiment, tractor unit 40 would have flexible couplings 26 upon both front and rear ends 36 and 38 (as in FIG. 3).

Figure 3:
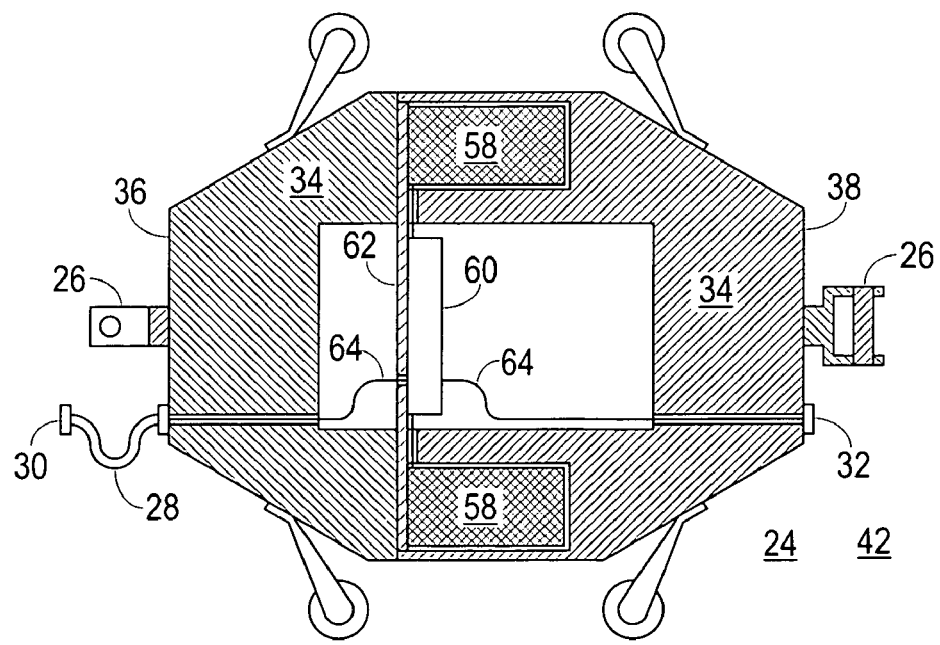
FIG. 3 shows a simplified cross-sectional view of a transmission unit for the inspection system of FIG. 1 in accordance with a preferred embodiment of the present invention.

In alternative embodiments where tractor unit 40 has flexible couplings 26 upon both front and rear ends 36 and 38, intra-unit wiring 56 continues through tractor unit 40 to electrical coupling 28 affixed to front end 36 (as in FIG. 3).

FIG. 3 shows a simplified cross-sectional view of RFT transmission unit 42 for RFT inspection system 20 in accordance with a preferred embodiment of the present invention. The following discussion refers to FIGS. 1 and 3.

RFT transmission unit 42 contains an excitation coil 58 configured to produce a magnetic field (discussed hereinafter) within pipeline 22. Desirably, excitation coil 58 is substantially concentric with pipeline 22. Those skilled in the art will appreciate that other embodiments of excitation coil may be utilized without departing from the spirit of the present invention.

In order to produce the strong magnetic field desirable for RFT inspection methodology, excitation coil 58 is desirably a high-current device. Therefore, transmission unit 42 also contains a current driver 60 electrically connected to excitation coil 58.

Excitation coil 58 and current driver 60 together generate a significant amount of heat when in operation. This heat is passed to a heat sink 62 which is coupled to both excitation coil 58 and current driver 60, and then to body 34 of transmission unit 42. This heat is the dissipated within pipeline 22. To facilitate the transfer of heat, it is desirable that the body of transmission unit 42 be more massive than other modular units 24. However, this is not a requirement of the present invention. Other forms of body 34 for transmission unit 42 may be used without departing from the spirit of the present invention.

Power and/or signals for transmission unit 42 pass through receptacle 32. Intra-unit wiring 64 couples receptacle 32 to current driver 60, excitation coil 58, and any other electrical/electronic devices within transmission unit 42. Intra-unit wiring 64 continues through transmission unit 42 to electrical coupling 28 and plug 30 affixed to front end 36 to pass power and/or signals for leading modular units 24.

Desirably, intra-unit wiring 64 is suitably shielded to limit electrical interference with signals present in modular units 24 and in intra-unit wiring 64 itself.

In FIG. 1, transmission unit 42 is the second modular unit 24. As the second modular unit 24, transmission unit 42 has flexible couplings 26 upon both front and rear ends 36 and 38. Using transmission unit 42 as the second modular unit 24 is exemplary, and is not a requirement of the present invention. In an alternative embodiment transmission unit 42 may be the first modular unit 24. In this alternative embodiment, transmission unit 42 would have flexible coupling 26 only upon rear end 38.

Figure 4:
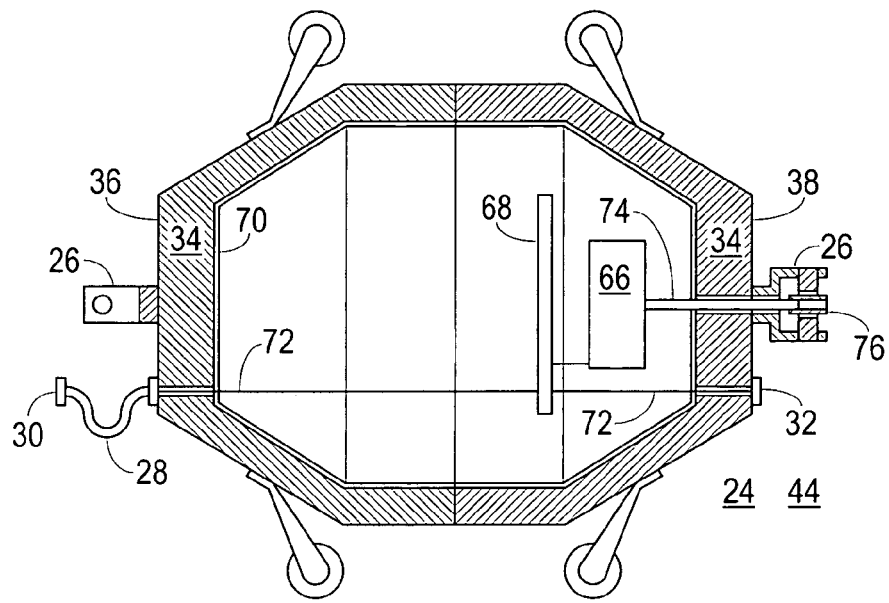
FIG. 4 shows a simplified cross-sectional view of a motor unit for the inspection system of FIG. 1 in accordance with a preferred embodiment of the present invention.

FIG. 4 shows a simplified cross-sectional view of motor unit 44 for RFT inspection system 20 in accordance with a preferred embodiment of the present invention. The following discussion refers to FIGS. 1 and 4.

Motor unit 44 contains a rotational motor 66 configured to rotate reception coils within reception unit 46 (discussed hereinafter). Desirably, motor unit 44 also contains a motor control 68 electrically coupled to motor 66.

Because rotational motor 66 is a potential source of electrical noise (discussed in more detail hereinafter), it is desirable that motor unit 44 be shielded. Motor unit 44 is therefore desirably lined with a conductive shield 70. By being conductive, shield 70 limits severely the amount of electronic noise radiated into pipeline by motor 66.

If shield 70 is also formed of magnetically conductive material, such as Mumetal, then magnetic fields generated by rotational motor 66 may also be constrained from entering pipeline 22. This is desirable, as magnetic fields induced by rotational motor 66 may produce additional interference for the reception coils (discussed hereinafter).

In other embodiments (not shown), additional devices (e.g., a motor control circuit) may be incorporated without departing from the spirit of the present invention.

Power and/or signals for motor unit 44 pass through receptacle 32. Intra-unit wiring 72 couples receptacle 32 to rotational motor 66 and any other electrical/electronic devices within motor unit 44. Intra-unit wiring 72 continues through motor unit 44 to electrical coupling 28 and plug 30 affixed to front end 36 to pass power and/or signals for leading modular units 24.

Desirably, intra-unit wiring 72 is suitably shielded to limit electrical interference with signals present in modular units 24 and in intra-unit wiring 72 itself.

It is a task of rotational motor 66 to rotate the reception coils (discussed hereinafter) in reception unit 46 relative to the wall of pipeline 22.

Additionally, rotational motor 66 is desirably a variable-speed motor, thereby allowing motor 66 to rotate the reception coils relative to the wall of pipeline 22 at any desired speed. The use of a variable-speed motor 66 provides the ability to better cover the inner surface of pipeline 22 at varying speeds of passage through pipeline 22. The effects of variable speed are discussed in more detail hereinafter.

Rotational motor 66 is configured to rotate the reception coils (discussed hereinafter) within reception unit 46. Because of noise considerations, motor unit 44 is independent of reception unit 46 in the preferred embodiment of the Figures. That is, motor unit 44 and reception unit 46 are separate modular units 24. Since motor 66 is in motor unit 44, and the reception coils to be rotated by motor 66 are in reception unit 46, it is necessary to pass the rotation of motor 66 out of motor unit 44.

In the embodiment of the Figures, this is accomplished by a motor shaft 74 (i.e., the shaft of rotational motor 66 or an extension thereof) passing through rear end 38 of body 34 and into flexible coupling 26. In this embodiment, flexible coupling 26 is configured to pass motor shaft 74 (i.e., flexible coupling 26 has a hole through it). Within a central portion of flexible coupling 26, a flexible shaft coupling 76 is coupled to motor shaft 74.

In an alternative embodiment (not shown), rotational motor 66 may reside within reception unit 46, i.e., motor unit 44 may be integral with reception unit 46. In this embodiment, motor shaft 74 may couple directly to the reception coils, thereby eliminating the need for flexible shaft coupling 76 and the necessary mechanical components associated therewith. While this embodiment significantly decreases the complexity of the motor-to-coil coupling, the proximity of motor 66 to the reception coils increases the potential for electrical noise interference. Adequate shielding should therefore be introduced between motor 66 and the reception coils. Those skilled in the art will appreciate that the use of this or other alternative embodiments does not depart from the spirit of the present invention.

Figure 5:
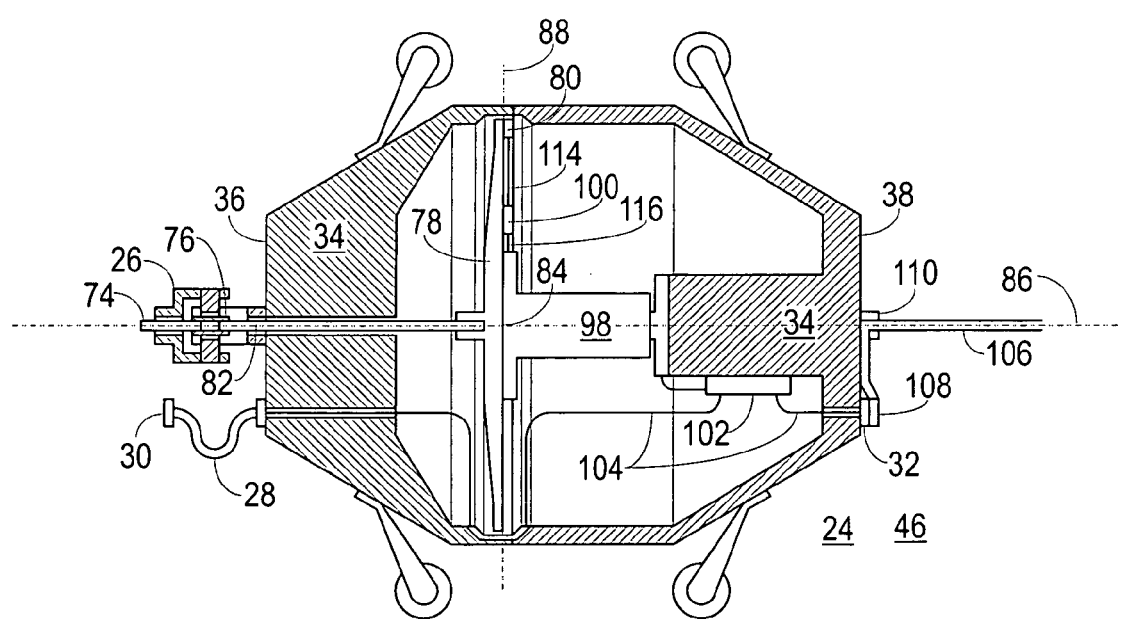
FIG. 5 shows a simplified cross-sectional view of a reception unit for the inspection system of FIG. 1 in accordance with a preferred embodiment of the present invention.
Figure 6:
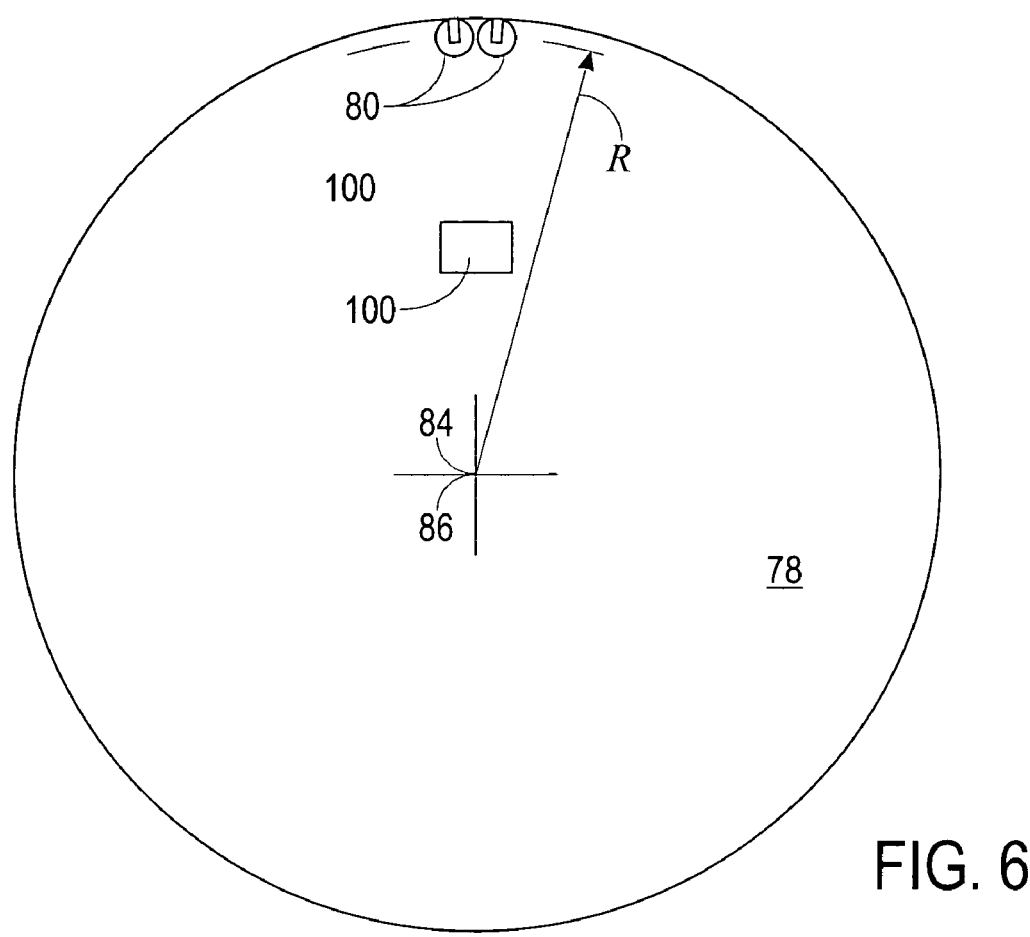
FIG. 6 shows a surface view of a rotational mount for the reception unit of FIG. 5 in accordance with a preferred embodiment of the present invention.
Figure 7:
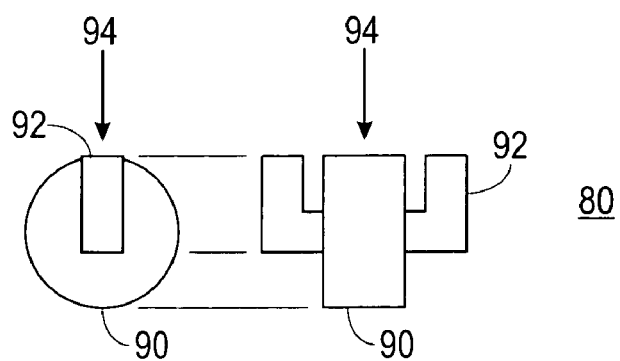
FIG. 7 shows side and front views of reception coils for the reception unit of FIG. 5 in accordance with a preferred embodiment of the present invention.

FIG. 5 shows a simplified cross-sectional view of reception unit 46 for RFT inspection system 20, FIG. 6 shows a surface view of a rotational mount 78 for reception unit 46, and FIG. 7 shows side and front views of reception coils 80 for reception unit 46 in accordance with a preferred embodiment of the present invention. The following discussion refers to FIGS. 1, 5, 6, and 7.

As discussed hereinbefore, motor shaft 74 couples to flexible shaft coupling 76 within a central portion of flexible coupling 26. A mount shaft 82 also couples to flexible shaft coupling 76 with the central portion of flexible coupling 26. Mount shaft 82 passes through front end 36 of body 34 of RFT reception unit 46 and fixedly couples to rotational mount 78. In this manner, rotational motor 66 (FIG. 4) is rotationally coupled to rotational mount 78 through flexible coupling 26. Reception coils 80 are affixed to rotational mount 78. Therefore, rotation of motor 66 causes rotation of reception coils 80.

In an alternative embodiment (not shown), all or a portion of the combination of motor shaft 74, flexible shaft coupling 76, and mount shaft 82 may be replaced by a flexible shaft to pass rotation from rotational motor 66 to rotational mount 78. The use of this alternative embodiment or any other method of transferring rotation does not depart from the spirit of the present invention.

Rotational mount 78 is configured to rotate about a center of rotation 84 substantially coincident with an axis 86 of reception unit 46, and in a plane of rotation 88 substantially perpendicular to axis 86.

In the preferred embodiment, reception coils 80 constitute at least one pair of adjacent, substantially identical differentially coupled reception coils 80 affixed to rotational mount 78 proximate an edge of rotational mount 78 at equal radial distances R from center of rotation 84, i.e., from axis 86. Each reception coil 80 is desirably made up of a coil 90 wrapped around a U-shaped core 92, with an open end 94 of U-shaped core 92 oriented away from axis 86.

The use of U-shaped cores 92 produces the greatest sensitivity for the detection of small flaws. In an alternative embodiment (not shown), it may be desirable to detect large flaws (e.g., large-area corrosion). In this embodiment, it may be preferable to use cores of other shapes, or to omit the cores completely.

It is desirable that reception coils 80 scan pipeline 22 as close as is practical to achieve a maximum signal strength (discussed hereinafter). Modular units 24 clear the inside wall of pipeline 22 by distance S of at least 12.5 mm (0.5 inch) to facilitation negotiation through pipeline 22. Therefore, reception coils 80 scan pipeline 22 from a distance greater than 12.5 mm (0.5 inch). Since rotational mount 78 and reception coils 80 must clear body 34 of reception unit 46, reception coils 80 are typically no closer than 19 mm (0.75 inch) to pipeline 22, and desirably 25-32 mm (1.0-1.25 inch) from pipeline 22.

In the exemplary embodiment of the Figures, rotary mount 78 is depicted as a disk or plate. This is not a requirement of the present invention. Other shapes for rotary mount 78 may be used without departing from the spirit of the present invention. Desirably, rotary mount 78 is suitably balanced, regardless of its shape, so as to prevent unnecessary vibration. Such vibration may interfere with the reception of a suitable signal due to vibratory modulation.

Pipeline 22 has an inner diameter D. In order to minimize eddy current effects, it is desirable that reception coils 80, i.e., plane of rotation 88, be located at a distance D at least two pipeline diameters d from a near edge 96 of excitation coil 58, i.e., $D \geq 2d$. Also, to maintain reception of a rapidly dwindling magnetic field (discusses hereinafter), it is desirable that reception coils 80 be located not more that three pipeline diameters d from near edge 96, i.e., $2d \leq D \leq 3d$. Those skilled in the art will appreciate that these distances are not absolute. Minor variations from these distances do not depart from the spirit of the present invention.

It will also be appreciated that these distances affect and to some degree determine the configuration of RFT inspection system 20. That is, using modular units 24 capable of passing through and negotiating curves, fittings, and debris #23 within pipeline 22, it is unlikely that RFT transmission unit 42 would be adjacent to RFT reception unit 46, as this would render reception distance D less than twice pipeline inner diameter d.

In the exemplary embodiment of the Figures, and for the sake of clarity, only one pair of adjacent differentially coupled reception coils 80 is depicted mounted upon rotational mount 78. In practice, any desired number of pairs of reception coils 80 may be mounted upon rotary mount 78.

In order for a signal from reception coils 80 to pass from rotational mount 78 to the non-rotation portions of reception unit 46, a slip ring assembly 98 is used. In the preferred embodiment, slip ring assembly 98 is desirably a low-noise fiber brush slip ring assembly. This is not a requirement, however, and other methodologies known to those skilled in the art (e.g., rotary transformers and/or RF transmission) may be used without departing from the spirit of the present invention.

Even the best of slip rings introduce electrical noise. The output of reception coils 80 is very low, and may be compromised by slip-ring noise. Therefore, a differential instrumentation amplifier 100 for each pair of reception coils 80 is also mounted upon rotational mount 78. Each instrumentation amplifier 100 is electrically coupled to its respective pair of adjacent differentially coupled reception coils 80. The use of differentially coupled reception coils 80 and differential instrumentation amplifiers 100 significantly reduces sensitivity to "common-mode" electrical noise. Therefore, the outputs of differential instrumentation amplifiers 100 are amplified signals less susceptible to slip ring and other electrical noises.

In addition, biasing circuits, line drivers, etc. (not shown) associated with instrumentation amplifiers 100 may also be mounted upon rotary mount 78. By mounting these auxiliary components on rotational mount 78, a further reduction in the effects of slip-ring noise is achievable. However, this is not a requirement of the present invention. Other methodologies may be used without departing from the spirit of the present invention.

The outputs of differential instrumentation amplifiers 100 may itself be differential. Those skilled in the art will be aware that the use of differential signals at all points in system 20 will significantly improve performance. However, the use of differential signals throughout system 20 is not a requirement of the present invention.

Within reception unit 46, the output of slip rings 98, i.e., the robust outputs of differential instrumentation amplifiers 100, may pass to other electronics 102 for further processing, digitization, and/or modulation. Electronics 102 represent various forms of signal processing well known to those skilled in the art, and may vary depending upon the instrumentation used with system 20.

Power and/or signals for RFT reception unit 46 pass through receptacle 32. Intra-unit wiring 104 couples receptacle 32 to electronics 102, slip ring assembly 98, and any other electrical/electronic devices within reception unit 46. Intra-unit wiring 104 continues through reception unit 46 to electrical coupling 28 and plug 30 affixed to front end 36 to pass power and/or signals for leading modular units 24.

Desirably, intra-unit wiring 104 is suitably shielded to limit electrical interference with signals present in modular units 24 and in intra-unit wiring 104 itself.

In the exemplary embodiment of the Figures, power and/or signals for RFT inspection system 20 pass through electrical cable 106 and plug 108. Plug 108 mates with receptacle 32 and allows electrical cable to be connected and disconnected at need. This aids in the insertion and extraction of system 20 into and out of pipeline 22.

Desirably, electrical cable 106 is suitably shielded to limit electrical interference with signals present in modular units 24 and in electrical cable 106 itself.

While the exemplary embodiment of the Figures depicts electrical cable 106 coupled to rear end 38 of reception unit 46, this is not a requirement of the present invention. Electrical cable 106 may couple to any of modular units 24, depending upon the specific configuration of system 20, that is the last modular unit 24. That is, electrical cable 106 couples to the end of system 20, whatever the configuration.

Electrical cable 106 serves as an umbilical for system 20. As system 20 traverses pipeline 22, electrical cable 106 trails behind and provides communication with power source(s) and instrumentation (not shown) external to pipeline 22.

Since electrical cable 106 is coupled to rear end 38 of the last modular unit 24, it is desirable that electrical cable be reinforced to allow electrical cable to draw system 20 backward through pipeline 22 in the event of a jam or for withdrawal. However, this is not a requirement of the present invention.

Operation of RFT Inspection System

Figure 8:
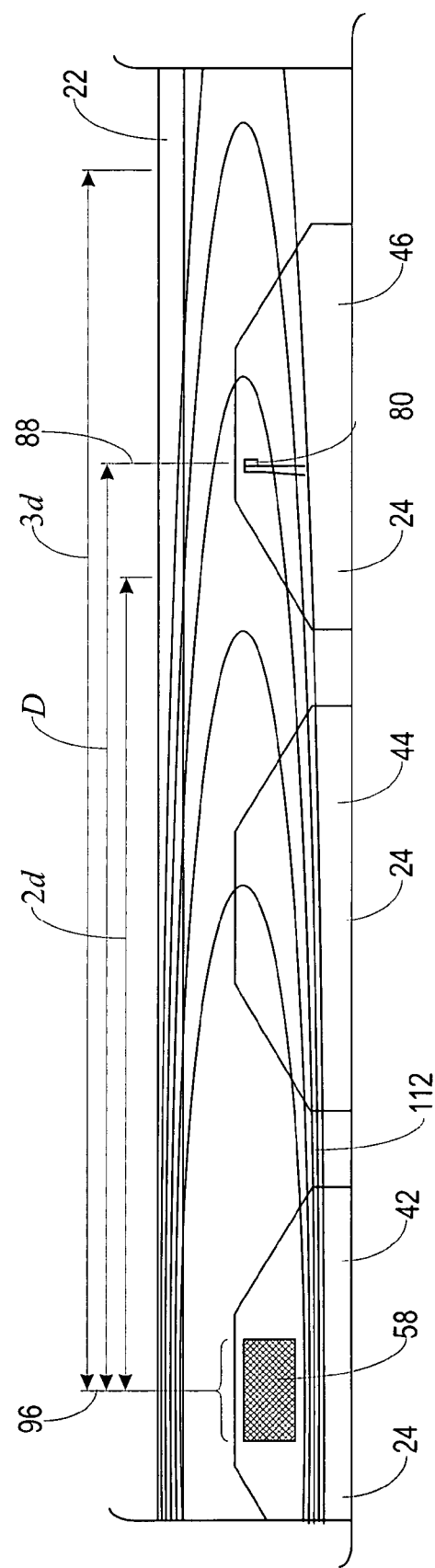
FIG. 8 shows a magnetic field between an excitation coil in the transmission unit of FIG. 3 and reception coils in the reception unit of FIG. 5 in accordance with a preferred embodiment of the present invention.

FIG. 8 shows a magnetic field 112 between excitation coil 58 in transmission unit 42 and reception coils 80 in reception unit 46 of RFT inspection system 20 in accordance with a preferred embodiment of the present invention. The following discussion refers to FIGS. 1, 2, 3, 4, 5, and 8.

For operation, RFT inspection system 20 is assembled and inserted into pipeline 22. In the exemplary embodiment of the Figures, tractor unit 40 is inserted into pipeline 22, RFT transmission unit 42 is coupled to tractor unit 40 and inserted into pipeline 22, motor unit 44 is coupled to RFT transmission unit 42 and inserted into pipeline 22, RFT reception unit 46 is coupled to motor unit 44 and inserted into pipeline 22, and electrical cable 106 is coupled to RFT reception unit 46.

Electrical cable 106 is appropriately connected to power source(s) and instrumentation (not shown) external to pipeline 22. The scanning data collected by reception coils 80, after amplification and internal processing discussed hereinbefore, is communicated via electrical cable 106 to the external instrumentation for processing and storage. This processing may be in accordance with conventional RFT techniques known to those of ordinary skill in the art. The scanning data may be augmented by rotational data collected by a rotational encoder and/or position sensor within RFT inspection system 20. Other data, such as video data from fore- and/or aft-mounted cameras, may also be included.

Power is applied to RFT inspection system 20.

Drive motor 48 within tractor unit 40 activates and causes system 20 to pass through pipeline 22.

Current driver 60 excites excitation coil 58 within RFT transmission unit 42 to produce magnetic field 112 within pipeline 22.

Rotational motor 66 within motor unit 44 rotates rotational mount 78 through motor shaft 74, flexible shaft coupling 76, and mount shaft 82, thereby rotating the pair of adjacent differentially coupled reception coils 80 relative to the wall of pipeline 22.

Rotating reception coils 80 detect magnetic field 112 and produce a differential detection signal 114 in response thereto. A flaw within pipeline 22 causes an uncharacteristic perturbation of magnetic field 112. This localized perturbation is detected differently by each reception coil 80 in the pair of differentially coupled reception coils 80 as the pass near the flaw.

Differential detection signal 114 is then amplified by differential instrumentation amplifier 100 to produce amplified signal 116. Amplified signal 116 is a robust signal 116, i.e., is relatively immune to noise interference. Robust signal 116 passes through slip ring assembly 98, is further processed by electronics 102 and exits system 20 and pipeline 22 via intra-unit wiring 104 and electrical cable 106. Instrumentation (not shown) external to pipeline 22 processes robust signal 116 and interprets the status of pipeline 22.

Desirably, robust signal 116 is fed back to current driver 60 in RFT transmission unit 42 via reception-unit wiring 104, a first flexible electrical coupling 28, motor-unit wiring 72, a second flexible electrical coupling 28, and transmission-unit wiring 64. This feedback of detection signal 114 (i.e., robust signal 116) allows current driver 60 and excitation coil 58 to compensate for variations in magnetic field 112 due to curves, fittings, and debris #23 within pipeline 22. The result is that an average amplitude of detection signal 114 is substantially constant throughout pipeline 22. Those skilled in the art will appreciate that the phrase "average amplitude" used herein is meant to mean "substantially the same signal amplitude over a significant interval." "Average" is not meant to imply and should not be taken to imply an arithmetic mean, a geometric mean, or any other mathematical "average."

Tractor unit 40 propels RFT inspection system 20 through pipeline 22 at a given speed. Motor 44 rotates reception coils 80 at a given speed. Therefore, the track of reception coils 80 describes a helix within pipeline 20. It is desirable that this helix be closed but not overlapping, i.e., complete coverage. That is, the path scanned by reception coils 80 on one cycle abuts but does not significantly overlap the path scanned on a previous cycle. In this manner, pipeline 22 is thoroughly inspected without wasted processing. That is, the closed helical scan pattern of reception coils 80 can detect latitudinal (transverse), longitudinal, and point flaws in pipeline 22.

Complete coverage may best be implemented by causing either drive motor 48, rotational motor 66, or both, to be variable speed. For reasons of economy and efficiency, rotational motor 66 is a variable-speed motor in the preferred embodiments. Automatic complete coverage may be obtained by using either feedback from drive motor 48 or a motion detection sensor (not shown) to control the rotational speed of motor 66 through motor control 68. This is not a requirement of the present invention. Other methods of rotational speed control may be employed without departing from the spirit of the present invention.

Detection signal 114 from reception coils 80 is very weak. In a typical application, the differential signal from reception coils 80 is on the order of 10 nv ($1/100^{th}$ of a microvolt). This makes detection signal 114 susceptible to electrical noise. By using a pair of reception coils 80 and electrically coupling them differentially, a significant rejection of common-mode noise is obtained.

In addition, by differentially coupling reception coils 80, they are better able to detect abrupt changes in magnetic field 112. These abrupt changes are characteristic of flaws in pipeline 22. Slow changes in magnetic field 112 also occur, but are not normally associated with flaws.

Also, by suppressing electromagnetic noise from known sources within RFT inspection system 20 itself, e.g., by the aforementioned shielding of tractor unit 40 and motor unit 44, a further reduction in noise is obtained. Other noise-reducing techniques not covered herein may be incorporated without departing from the spirit of the present invention.

In summary, the present invention teaches remote-field testing (RFT) pipeline inspection system 20 and method of operation thereof. System 20 detects latitudinal, longitudinal, and point flaws in pipeline 22, and provides robust detection signal 116.

Although the preferred embodiments of the invention have been illustrated and described in detail, it will be readily apparent to those skilled in the art that various modifications may be made therein without departing from the spirit of the invention or from the scope of the appended claims.

What is claimed is:

1. A system for inspecting a pipeline having an inner diameter d, said system comprising a plurality of modular units configured to pass through said pipeline, wherein each of said modular units is flexibly coupled to an adjacent modular unit, and wherein said plurality of modular units comprises:

a remote-field testing (RFT) transmission unit comprising an excitation coil configured to excite a magnetic field within said pipeline; and an RFT reception unit comprising a plurality of reception coils configured to rotate within said reception unit and relative to said pipeline and configured to detect said magnetic field within said pipeline at a reception distance D from said excitation coil, where $D \geq 2d$.

2. A system as claimed in claim 1 wherein said excitation coil is substantially concentric with said pipeline.

3. A system as claimed in claim 1 wherein each of said modular units comprises a substantially rigid body.

4. A system as claimed in claim 1 wherein said plurality of modular units additionally comprises a tractor unit configured to propel said system through said pipeline from within said pipeline.

5. A system as claimed in claim 1 wherein said excitation coil and said reception coils are positioned on average no closer than 12.5 mm (0.5 inch) from an inside wall of said pipeline.

6. A system as claimed in claim 1 wherein:
said plurality of reception coils produces a detection signal in response to said magnetic field;
said RFT reception unit additionally comprises an instrumentation amplifier coupled to one of said plurality of reception coils and configured to amplify said detection signal; and
said RFT transmission unit additionally comprises a current driver electrically coupled to one of said plurality of said reception coils and said instrumentation amplifier, electrically coupled to said excitation coil, and configured to produce said magnetic field so that an average amplitude of said detection signal is substantially constant.

7. A system as claimed in claim 1 wherein:
said plurality of reception coils comprises a pair of adjacent differentially coupled reception coils;
said pair of reception coils produces a differential detection signal in response to said magnetic field; and
said RFT reception unit additionally comprises a differential instrumentation amplifier coupled to said pair of reception coils and configured to amplify said differential detection signal to produce an amplified signal.

8. A system as claimed in claim 7 wherein each of said pair of reception coils comprises a U-shaped core having an open end oriented away from an axis of said RFT reception unit.

9. A system as claimed in claim 7 wherein each of said pair of reception coils is at a common radial distance R from an axis of said RFT reception unit.

10. A system as claimed in claim 7 wherein said pair of reception coils is affixed to a rotational mount having a center of rotation coincident with an axis of said RFT reception unit.

11. A system as claimed in claim 10 wherein said rotational mount has a plane of rotation substantially perpendicular to said axis.

12. A system as claimed in claim 10 wherein said instrumentation amplifier is affixed to said rotational mount and configured to rotate with said pair of reception coils.

13. A system as claimed in claim 1 additionally comprising a motor coupled to and configured to rotate said plurality of reception coils.

14. A system as claimed in claim 13 wherein said motor is a variable-speed motor.

15. A system as claimed in claim 13 wherein said plurality of modular units additionally comprises a motor unit comprising said motor.

16. A system as claimed in claim 1 wherein each of said modular units is configured to be coupled to an adjacent modular unit by a detachable electrical connection.

17. A remote-field testing (RFT) method of inspecting a pipeline having an inner diameter d, said RFT method comprising:
incorporating, within said pipeline, a transmission unit comprising an excitation coil;
incorporating, within said pipeline, a reception unit comprising a plurality of reception coils at a reception distance D from said excitation coil, where $D \geq 2d$;
exciting said excitation coil to produce a magnetic field within said pipeline;
rotating, coincident with said exciting activity, said plurality of reception coils within said reception unit and relative to said pipeline;
detecting, during said rotating activity, said magnetic field; and
producing a detection signal in response to said magnetic field.

18. An RFT method as claimed in claim 17 wherein:
said rotating activity rotates a pair of adjacent differentially coupled reception coils relative to said excitation coil; and
said producing activity produces a differential detection signal in response to said magnetic field.

19. An RFT method as claimed in claim 18 wherein said incorporating activity comprises:
providing each of said reception coils with a U-shaped core having an open end; and
orienting said reception coils so that said open end points away from an axis of said reception unit.

20. An RFT method as claimed in claim 18 additionally comprising affixing said pair of reception coils to a rotational mount having a center of rotation coincident with an axis of said reception unit and having a plane of rotation substantially perpendicular to said axis.

21. An RFT method as claimed in claim 20 wherein:
said method additionally comprises incorporating a motor unit independent of said reception unit and comprising a motor; and
rotationally and flexibly coupling said motor to said rotational mount.

22. A system for inspecting a pipeline having an inner diameter d, said system comprising:
a remote-field testing (RFT) transmission unit configured to pass though said pipeline, said RFT transmission unit comprising: a current driver; and
an excitation coil substantially concentric with said pipeline, coupled to said current driver, and configured to generate and transmit a magnetic field into said pipeline in response to said current driver;
an RFT reception unit flexibly coupled to said RFT transmission unit and configured to pass through said pipeline, said RFT reception unit comprising:
a pair of adjacent differentially connected reception coils, configured to detect said magnetic field at a reception distance D from said excitation coil, where $2d \leq D \leq 3d$, and configured to generate a differential detection signal from said magnetic field;
an instrumentation amplifier coupled to said pair of reception coils and configured to amplify said differential detection signal to produce an amplified signal; and
a motor unit configured to pass through said pipeline, coupled to said RFT reception unit, and configured to rotate said pair of reception coils and said instrumentation amplifier;
a tractor unit flexibly coupled to one of said RFT transmission unit, said RFT reception unit, and said motor unit, and configured to propel said system through said pipeline;
an electrical cable coupled to one of said RFT transmission unit, said RFT reception unit, said motor unit, and said tractor unit, wherein said electrical cable is configured to provide electrical power for said system.

* * * * *